United States Patent [19]

Hansen et al.

[11] 4,355,018

[45] Oct. 19, 1982

[54] ASSAY FOR VITAMIN $B_{12}$

[75] Inventors: Hans J. Hansen, Allendale, N.J.; Gustavo Reynoso, Endwell, N.Y.

[73] Assignees: Hoffmann-La Roche Inc., Nutley, N.J.; The Ideal Wilson Medical Center, Johnson City, N.Y.

[21] Appl. No.: 151,796

[22] Filed: May 21, 1980

[51] Int. Cl.$^3$ ............................................. G01N 33/56
[52] U.S. Cl. ....................................... 424/1; 23/230 B; 424/12
[58] Field of Search ...................... 424/1, 12; 23/230 B

[56] References Cited

U.S. PATENT DOCUMENTS 3,937,799  2/1976  Lewin et al. ............................. 424/1
4,146,602  3/1979  Gutcho et al. ........................ 424/12
4,188,189  2/1980  Allen .................................. 23/230 B
4,209,614  6/1980  Bernstein et al. ..................... 424/12

Primary Examiner—Christine M. Nucker
Attorney, Agent, or Firm—Jon S. Saxe; George M. Gould; John B. Wilson

[57] ABSTRACT

A highly specific assay for plasma vitamin $B_{12}$ levels in humans is disclosed. The assay employs intrinsic factor preparations obtained from mouse or rat stomachs, which intrinsic factors are free of R-protein and thus react specifically with vitamin $B_{12}$ in a competitive binding assay. Detection of vitamin $B_{12}$ levels is utilized in the diagnosis of several clinical disorders, such as pernicious anemia, a disease state which results in reduced circulating levels of vitamin $B_{12}$ in the blood.

8 Claims, No Drawings

ASSAY FOR VITAMIN $B_{12}$

BACKGROUND OF THE INVENTION

Early procedures for the assay of vitamin $B_{12}$ (also referred to as cobalamin or cyanocobalamin) employed bacterial species, such as Euglena gracius or lactobacillus leichmannie which lacked the intrinsic ability to synthesize vitamin $B_{12}$. Such microbiological assays determined vitamin $B_{12}$ levels in an extract of a plasma sample from a human subject by measuring the growth of the vitamin $B_{12}$ sensitive organism in a vitamin $B_{12}$ free medium to which a known amount of the plasma sample extract had been added. Since the growth of the sensitive organism was, within certain limits, proportional to the vitamin $B_{12}$ concentration in the medium, it was possible by measuring a suitable growth parameter, such as optical density of the test solution after incubation for a selected period of time and at a certain selected temperature, and comparing this parameter to values observed by running the same test with samples containing different, known concentrations of vitamin $B_{12}$ to determine the concentration of vitamin $B_{12}$ in the plasma sample extract.

The microbiological assay, while being a selective and sensitive assay, is difficult to perform requiring sterile techniques and thus requires highly skilled technicians. Moreover, it is difficult to maintain colonies of the required vitamin $B_{12}$ sensitive microorganisms. Additionally, results are not available for several days, and the tests cannot be carried out on patients who are taking antibiotics or other drugs. Thus when radioreceptor assays were subsequently developed, the art rapidly dropped the microbiological methodology and switched to the more convenient assay.

The radioreceptor assay utilized competitive binding inhibition by vitamin $B_{12}$ contained in a patient's plasma sample to the binding of known concentrations of a radiolabeled vitamin $B_{12}$ derivative, i.e., $^{57}$Co-vitamin $B_{12}$ to receptor sites on an intrinsic factor (IF) preparation. The intrinsic factor preparations were derived from the stomachs of higher mammals, primarily hogs. These preparations were impure in the sense that they were contaminated with substantial, even major amounts of R-proteins. Unlike intrinsic factor, which binds vitamin $B_{12}$ in a highly selective manner, the R proteins have non-specific binding characteristics and will bind to the natural analogs of vitamin $B_{12}$ which are closely related structurally to vitamin $B_{12}$ but which are biologically inactive.

This contamination of intrinsic factor with R-protein was not considered by the art to affect the assay procedure, since the natural analogs of vitamin $B_{12}$ were known to be present normally in the human gut but were not believed to be absorbed and present in the blood stream and tissue. However, in a paper by Kolhouse, et al., in The New England Journal of Medicine, Vol. 299, No. 15, pp. 785-789 (Oct. 12, 1978), it was demonstrated that such biologically inactive analogs do, in fact, naturally exist in the human blood stream. These analogs were measured as true cobalamin by the commercially available radioassay for vitamin $B_{12}$, and this was believed to be the reason for observed discrepancies wherein serum $B_{12}$ values obtained by radioassays were consistently higher than those obtained with microbiologic assays.

The clinical implications of these discrepancies were noted by Cooper and Whitehead in the same issue of The New England Journal of Medicine at pp. 816-818 in a paper entitled, "Evidence That Some Patients With Pernicious Anemia Are Not Recognized By Radiodilution Assay For Cobalamin In Serum". These authors in their discussion of the situation make the following statement:

"This reliability [of the microbiological assay] appears not be be true of the radiodilution assays tested. The data show that whereas these assays give quantitative and reproducible results, they did not detect all patients with clinically proved deficiency of cobalamin . . . .

These data are of concern because of the widespread use of radiodilution assay and the use of assay for cobalamin in serum to screen for deficiency of the vitamin . . . . It appears that analogues of cobalamin are present in human serum and plasma and that these analogues bind effectively to non-intrinsic-factor cobalamin binders in most commercial preparations of 'intrinsic factor.' . . . The well documented specificity of authentic intrinsic factor for cobalamin itself indicates that radiodilution assays using pure authentic intrinsic factor would provide a reliable method for determining cobalamin in serum."

After these two papers were published there has been intensive activity by commercial vitamin $B_{12}$ radioassay manufacturers to modify their kits to try to overcome these serious problems. As described by Kubasik, et al., Clin. Chem. 26/5, 598(1980), there have been two basic approaches to achieve a solution:

"1. Negate the R-protein binding sites: This can be accomplished by flooding the IF-R protein combination binder with an analog such as cobinamide. Cobinamide will not bind the IT, but will bind to R-proteins. If added in great excess (>100-fold), it will quench all the non-specific cobalamin binding sites 2. Purify the IF: IF concentrate can be purified by prolonged treatment with proteolytic enzymes, such as trypsine (E.C. 3.4.21.4) or chymotrypsin (E.C.-3.4.21.1), or both, or by affinity chromatography."

Evaluation of these approaches by the authors resulted in the following conclusion:

"From our data presented here, it appears that although the 'cobinamide'-blocked binder can be used, we agree . . . that pure or 'purified' IF would be the better choice of a binder, for analytical reasons. Any possible non-specific effects due to other binders would be eliminated."

Criteria which were employed in established purity of the intrinsic factor preparations were as follows:

1. Binding of bioactive cabalamin was completely inhibited when active IF was first incubated with antibody to IF.

2. Comparing binders in assays performed at acidic and basic pH, and at basic pH in the presence of cobalamin analogs. A purified IF preparation exhibits very low cobalamin binding ability at acidic pH, and the binding at basic pH will be little affected by the presence of cobalamin analogs.

3. Purified IF does not measure "cobinamide" (cyanohydroxycobinamide) even at extremely high concentrations.

DESCRIPTION OF THE INVENTION

The present invention relates to an improved radioassay for vitamin $B_{12}$ which is characterized in employing as the intrinsic factor preparation a saline extract of mouse or rat stomachs. Such mouse or rat derived intrinsic factor, unlike the intrinsic factor preparations derived from higher mannals, such as hog, is essentially free of R-protein. Thus the use of the mouse or rat derived intrinsic factor in radioassay for vitamin $B_{12}$ will not mask cobalamin deficiency in the assay subject, since these intrinsic factor preparations are specific for true cobalamin. Additionally, the use of mouse or rat derived intrinsic factor avoids the necessity of having to undertake the inefficient, time-consuming, and expensive purification procedures, such as affinity chromatography, required for intrinsic factor preparations obtained from other mammalian sources contaminated with R-protein. In a further aspect of the invention, it has been found that maximum efficiency in the assay procedure is obtained by carrying out extraction of the serum sample with cyanide buffer at pH 4.5 and carrying out the radioassay at a pH of 7.2.

Mouse and rat intrinsic factor preparations exhibit the properties of pure intrinsic factor without the necessity of undertaking the purification procedures. Thus, the intrinsic factor preparations used in the present invention will be greater than 98% inhibited in the binding of bioactive cobalamin when preincubated with antibody to intrinsic factor. Addition of 10,000 pg of cobinamide to an assay sample using the rat or mouse intrinsic factors does not result in any observable inhibition to the binding of true cobalamin. Finally, gel chromatography of the mouse or rat derived intrinsic factor preparation tagged with radiolabeled $B_{12}$ produces a single sharp peak corresponding to an apparent molecular weight of about 55,000. This peak is almost completely inhibited by preincubation with antibody to intrinsic factor.

The mouse and rat intrinsic factor preparations can be obtained from mouse or rat stomachs by procedures known per se. Thus, the mouse or rat stomachs can be homogenized in cold saline and the supernatant separated from the residual tissue mass by centrifugation or filtration. It is desirable that the resulting saline extract be adjusted to pH 10 with aqueous dilute base, such as an alkali hydroxide, preferably sodium hydroxide, to inactivate any pepsin which is present in the stomach and carried into the extract. Pepsin can cause degradation of the intrinsic factor unless inactivated by denaturation in base.

A representative preparation of mouse intrinsic factor is set forth below:

1 part (150 g) of clean minced mouse stomachs homogenized with 4 parts of phosphate buffered saline (pH 7.2) for 5 minutes at 4° C. in a Sorvall homogenizer. The homogenate is centrifuged for 30 minutes at 30,000 g and 4° C. The supernatent is decanted and adjusted to pH 10 with 1 N NaOH. After stirring for 20 minutes the pH is adjusted with 1 N HCl to 5.0. Centrifugation again at 30,000 g for 30 minutes to remove precipitate and the supernatant adjusted to pH 7.2 with 1 N NaOH.

The mouse or rat derived intrinsic factors can be utilized in any of the standard radioassay procedures for $B_{12}$ known in the art. A particularly preferred procedure is set forth below:

MOUSE INTRINSIC FACTOR VITAMIN $B_{12}$ PROCEDURE

A. Extraction of Endogenous Cabalamin from Serum

1. Pipet 0.5 ml of serum into a 12 ml "red-top" vacutainer tube.
2. Add 4.5 ml of cyanide buffer and mix well.
3. Cap the tube with the original stopper and pierce the stopper with a #22 blood-drawing needle, leaving the needle through the cap for venting purposes.
4. Place the tube in boiling water for 30 minutes.
5. Cool the tube by placing it in an ice-water bath.
6. Mix the contents rapidly in a vortex mixer. Complete mixing is important.
7. Remove the needle and centrifuge the tube at 1500×G for 20 minutes.
8. The appropriate control sera are extracted by a similar method.

B. Recovery Control of the Extraction Procedure

1. Pipet 0.5 ml of serum into a 12 ml "red-top" vacutainer tube.
2. Add 100 μl $^{57}$Co-Cyanocobalamin, (approximately 14,000 DPM).
3. Add 4.4 ml of cyanide buffer and mix well.
4. Proceed as in steps 3–7 of Extraction Procedure.
5. Pour the supernatant fluid from the extraction recovery into an appropriately labeled vacutainer tube. It is important to have the precipitate and the supernatant fluid in identical tubes. Keep both tubes, one containing the precipitate and the other the supernatant.
6. A recovery control is also needed for each of the control sera.

C. Ligand Assay

1. Prepare standard tubes in duplicate by mixing working standard and buffer as follows:

| Standard | Standard Buffer | Working Standard |
| --- | --- | --- |
| 0 | 1100 μl | 0 μl |
| 5 | 1100 | 5 |
| 10 | 1100 | 10 |
| 25 | 1075 | 25 |
| 50 | 1050 | 50 |
| 75 | 1025 | 75 |
| 100 | 1000 | 100 |
| 150 | 950 | 150 |
| NSB | 1100 | 0 |
| Total | 1100 | 0 |

2. Pipet 1.0 ml of the clear supernatant from the serum extraction into each of two 12×75 mm polystyrene tubes.
3. To each extract, add 100 μl of phosphate hydroxide solution.
4. To all tubes add 100 μl $^{57}$Co-B-12.
5. Mix the contents of all the tubes thoroughly.
6. To all the tubes except "Non-specific Binding" (NSB) and "Total" add 200 μl of mouse IF (1:1000 in 0.5 m phosphate buffer pH 7.2). To the Blank and Total, add 200 and 400 μl respectively of 0.5 m phosphate buffer pH 7.2.
7. Mix the contents in a vortex mixer.
8. Let the tubes stand for 30 minutes at room temperature.
9. To all the tubes, except "Total", add 200 μl of albumin-coated charcoal. The charcoal must be constantly mixed while it is being pipetted.
10. Mix each tube again briefly in a vortex.
11. Centrifuge the tubes at 1,500×G for 20 minutes.
12. Decant the supernatants into appropriately labeled tubes and place them in a gamma counter.
    a. Total
    b. Blank
    c. 'O' standard Reagents Cyanide buffer 0.2 m pH 4.6.

| A. CH₃COONa.3H₂O | 27.2 gm/L |
|---|---|
| B. CH₃COOH | 11.5 gm/L |

Mix 480 ml A and 520 ml B.
Adjust to pH 4.6 if necessary.
Add 1 ml of 0.4% KCN (40 mg/10 cc H₂O).
Acetate Buffer:
0.1 m pH 4.6 adjusted to pH 7.2 with phosphate/hydroxide solution.
Phosphate Buffer 0.5 m pH 7.2:

| A. Na₂HPO₄ | 35.5 gm/500 cc |
|---|---|
| B. Na₂HPO₄.H₂O | 34.5 gm/500 cc |

Mix to pH 7.2.

Phosphate/Hydroxide Buffer: Dissolve 3.8 gm NaOH/100 cc of pH 7.2 buffer. Titrate 10 ml of acetate-CN-extraction buffer with 1.0 ml PO₄/OH to pH 7.0–7.2 and adjust extraction buffer with NaOH or phosphate buffer if necessary.

Radioactive B$_{12}$: Amersham Searle (10 μCo/ml). Dilute 75 μl/10 cc with phosphate buffer, 0.5 m, pH 7.2.

Standard Vitamin B$_{12}$: Stock Vitamin B$_{12}$ obtained from Parke-Davis (Betalin) (100 μg Cyanocobalamin per ml).

Dilute 1:1000 to a concentration of 0.1 μg/ml in 0.5 M phosphate buffer, pH 7.2.

Prepare working standard (1 ng/ml) by diluting the above solution 1:1000 in 0.5 m phosphate buffer, pH 7.2.

Albumin Buffer: Dilute 2 ml of 22% bovine albumin to 15 ml with 0.5 m phosphate buffer, pH 7.2.

Mouse Intrinsic Factor: Dilute the mouse stomach extract 1:1000 with 0.5 m phosphate-albumin buffer pH 7.2.

Manual Calculations
1.

$$\text{Percent Bound} = \frac{\text{cpm supernatant } (e) - \text{cpm NSB}}{\text{cpm total}} \times 100$$

2. Plot percent bound versus pg B$_{12}$ per tube on linear graph paper, read unknowns verses standard curve, and multiply × 10 = pg/ml serum.

3. Recovery is calculated as follows:

$$\text{Recovery} = \frac{\text{cpm supernatant}}{\text{cpm precipitate } (f) + \text{cpm supernatant } (g)}$$

While the above procedure specifically employed mouse derived intrinsic factor, an analogous procedure can be employed for rat derived intrinsic factor or for that matter for intrinsic factor derived from any other mammalian species; stomach which is free of endogenous R-protein. Similarly while the radioligand described in the assay procedure was $^{57}$Co, it is possible to employ any other suitably radiolabeled cyanocobalamin, such as, for example, $^{125}$I labeled cyanocobalamin, in a manner known per se.

The affinity of the mouse intrinsic factor for cobalamin was determined by placing 200 μl of the primary dilution of mouse stomach extract in the final reaction tube, and it was found that was able to bind 50% of a trace amount of radiolabeled ligand. This amount of mouse stomach extract (MSE) was used for all subsequent experiments. Incubation of varying amounts of $^{57}$co-cobalamin with a constant amount of intrinsic factor allowed determination of the affinity constant (K) at pH 7.2 is $1.21 \times 10''$ liters per mole.

The titration data were confirmed by reacting a constant amount of intrinsic factor, 200 μl of the primary dilution with different concentrations of $^{57}$Co-cyanocobalamin for the purpose of determining the optimal amount of radioligand to be used in the assay. One hundred microliters of the working solution containing 45 picograms of radioactive cyanocobalamin was determined to be optimal. With the materials employed in the specific procedure above, this amount of $^{57}$Co-cyanocabalamin results in about 14,000 cpm in the "total" tube.

Standard curves for the inhibition assay useful in determining B$_{12}$ levels in clinical samples can be derived from the assay procedure described above. The concentrations of standards used in generating such standard curves should correspond with the amount of vitamin B$_{12}$ usually found in clinical samples. The final reaction conditions are: intrinsic factor, 200 μl of the primary dilution; radioactive ligand, 100 l of the working dilution; time 30 minutes; pH, 7.2; and non-radioactive standards, 5 to 150 picograms per tube, or the equivalent of 50 to 1,500 picograms of vitamin B$_{12}$ per ml of serum.

That intrinsic factor, free of "R" proteins, can be obtained from extracts of mouse stomach is supported by several experimental observations. When radiolabeled cobalamin is incubated with MSE under the conditions described above, and the mixture separated in a column packed with Sephadex G-150, the radioactive complex elutes as a single peak with an apparent molecular weight of 54,900. In the same column, the complex radiocobalamin-R-protein (human saliva or hog stomach extract concentrate) elutes with an apparent molecular weight of 101,000.

The formation of the radiocobalamin, mouse derived, intrinsic factor complex is completely inhibited by preincubation of the MSE with human anti-intrinsic factor antibody. The data are shown in Table 1:

TABLE 1

Inhibition of the Mouse Intrinsic Factor$^{57}$Co-Cobalamin Reaction by Human Anti-Intrinsic Factor Antibody

| | Intrinsic Factor Preparation | | Human Saliva | |
|---|---|---|---|---|
| Total Cobalamin in the Reaction Mixture (ng) | 15 | | 15 | |
| | (a) | (b) | (a) | (b) |
| Cobalamin Bound by the Binder Alone (ng) | 8.1 | 8.0 | 5.2 | 5.3 |
| Cobalamin Bound After Pre-Incubation With Antibody (ng) | 0.6 | 0.8 | 5.8 | 6.0 |
| | 0.5 | 0.7 | 6.2 | 6.2 |
| Cobalamin Bound by the Antiserum Alone (ng) | 0.8 | 0.6 | | |
| | 0.6 | 0.6 | | |
| Inhibition by Antiserum (a) = | 97.5% | | | |
| | 98.8% | | | |
| Antiserum (b) | 98.8% | | | |
| | 97.5% | | | |

When 15 nanograms of radiocobalamin are incubated with the appropriate amount of MSE, 8.1 nanograms of ligand are bound. Preincubation with two different preparations of antibody results in essentially complete inhibition of binding. By contrast, preincubation of human saliva with anti-intrinsic factor antibody shows that formation of the "R" protein $^{57}$Co-cobalamin complex is not inhibited by antibody.

When the antibody preincubated intrinsic factor-radiocabalamin mixture is passed through the Sephadex G-150 column as above, the peak at an apparent molecular weight of 54,900 is almost completely gone.

Cobinamide is useful as a model for the biologically inactive vitamin $B_{12}$ analogs. The ability of the analogs to inhibit the binding of true $B_{12}$ to the mouse intrinsic factor preparation can be conveniently studies by adding different concentrations of cobinamide to the reaction tubes containing MSE or human saliva and $^{57}$Co-cabalamin. The reaction conditions were as described above. The data demonstrated that 643,738 picograms of cobinamide are required to produce the same degree of inhibition (50%) as 60 picograms of cobalamin, thus indicating a calculated crossreactivity of less than 0.1% at pH 7.2. When the experiments are performed at pH 4.5, the figures are cobalamin, 49.1 pg/ml and cobinamide, 7.355 pg/ml for a calculated crossreactivity of 0.66%.

When human saliva is utilized in the same experiment in place of MSE, the results are in marked contrast. In such experiment 112 picograms of cobinamide produce the same degree of inhibition (50%) as 58.9 picograms of vitamin $B_{12}$ or a calculated crossreactivity of 52.6%. That the inhibition is competitive can be inferred from the similar and nearly parallel slopes of the inhibition curves, particularly in the saliva experiment.

Additional data on the inability of cobinamide to inhibit the mouse derived intrinsic factor-cobalamin reaction can be seen in Table 2 where the results of adding 10,000 pg of cobinamide to a control tube carried through the entire procedure are shown.

TABLE 2
Crossreactivity of Cobinamide With Cobalamine in the Ligand MIF Assay

| Day | B/Bo % | Recovery of 10,000 pg of Cobinamide as Cobalamine pg/ml |
|---|---|---|
| 1 | 98 | 9 |
| 2 | 99 | 5 |
| 4 | 101 | 0 |
| 7 | 98 | 10 |
| 8 | 99 | 5 |
| 9 | 97 | 24 |
| 10 | 104 | 0 |
| 11 | 101 | 0 |
| 15 | 95 | 24 |

Average Recovery 8.5 pg/ml
Crossreactivity 0.085%

The improved assay procedure of the present invention is of sufficient sensitivity so that 5 picograms of cabalamin in the reaction tube can be distinguished from zero with statistical significance, or a limit of sensitivity for the clinical assay of 50 pg/ml. Sensitivity data obtained from the subject assay is summarized below in Table 3.

TABLE 3
The Sensitivity of the Mouse Intrinsic Factor Ligand Assay for Serum Cobalamin Bound Counts Per Minute

| 0 | 50 Picograms per ml |
|---|---|
| 6514 | 5657 |
| 6130 | 5715 |
| 6274 | 5791 |
| 6252 | 5827 |

TABLE 3-continued
The Sensitivity of the Mouse Intrinsic Factor Ligand Assay for Serum Cobalamin Bound Counts Per Minute

| 0 | 50 Picograms per ml |
|---|---|
| Mean 6307 | 5761 |

$t = 6.128$
$p < .01$

The subject assay was run repetatively to determine the "within run" reproducibility. Results of these experiments are summarized below in Table 4.

TABLE 4
The "Within Run" Reproducibility of the Mouse Intrinsic Factor Ligand Assay by Serum Cobalamin

| Specimen # | Cobalamin, Picograms/ml | Specimen # | Cobalamin, Picograms/ml |
|---|---|---|---|
| 1 | 252.4 | 11 | 249.7 |
| 2 | 263.1 | 12 | 243.3 |
| 3 | 255.2 | 13 | 266.6 |
| 4 | 241.0 | 14 | 246.6 |
| 5 | 263.5 | 15 | 263.9 |
| 6 | 289.3 | 16 | 241.0 |
| 7 | 263.4 | 17 | 241.6 |
| 8 | 272.3 | 18 | 256.0 |
| 9 | 271.8 | 19 | 247.7 |
| 10 | 242.9 | 20 | 248.0 |

Mean 254.26
Standard Deviation 10.68
Coefficient of Variation 4.2%

Day-to-day variation and thus the precision of the test is indicated by the data collected in Table 5.

TABLE 5
Day-to-Day Reproduction of the MIF Ligand Method for Serum Cobalamin*

| | Sample 1 | | Sample 2 | |
|---|---|---|---|---|
| Day | Extraction Recovery % | Results in pg/ml | Extraction Recovery % | Results in pg/ml |
| 1 | 86 | 420 | 86 | 709 |
| 2 | 86 | 505 | 86 | 696 |
| 3 | 86 | 435 | 86 | 677 |
| 4 | 87 | 428 | 88 | 648 |
| | 86.2 (avg. recovery sample) | 444 ± 34 (avg. results) | 86.4 (avg. recovery sample) | 686 ± 24 (avg. results) |
| | Coefficient of variation | | Sample 1 = 7.7% Sample 2 = 3.5% | |

*All extractions at pH 4.6 and All assays at pH 7.2

The recovery of cobalamin added to normal serum and carried through the entire procedure is indicative of the accuracy achieved by the assay procedure. Results of such experiments are shown in Table 6.

TABLE 6
MIF Cobalamin Assay pH 7.2 The Recovery of Cobalamin Added to Normal Human Serum

| Added | Theoretical | Found | Recovery (Percentage) |
|---|---|---|---|
| | Endogenous Cobalamin | 252 pg/ml | |
| 100 | 352 | 345 | 93 |
| 200 | 452 | 458 | 103 |
| 400 | 652 | 632 | 95 |

Average Recovery 97
pH 4.5

| | Endogenous Cobalamin | 382 pg/ml | |
|---|---|---|---|
| 100 | 482 | 492 | 110 |
| 200 | 582 | 569 | 94 |

TABLE 6-continued

MIF Cobalamin Assay
pH 7.2
The Recovery of Cobalamin
Added to Normal Human Serum

| Added | Theoretical | Found | Recovery (Percentage) |
|---|---|---|---|
| 400 | 782 | 759 | 94 |

Average Recovery 99.33

A test kit which can be utilized in the practice of the improved radioassay method of the present invention comprises individual vials containing sufficient amounts of each reagent for multiple assays, such kit comprising:
1. one vial of radiolabeled cyanocabalamin solution, preferably $^{57}$Co-cyanocobalamin;
2. one vial of mouse or rat derived intrinsic factor in buffered solution;
3. one vial each of cobalamin standards at between 0 and 150 pg, preferably one vial each of 0. 5 pg, 10 pg, 25 pg, 50 pg, 75 pg, 100 pg and 150 pg standards.

Such kit may optionally also contain one or more of the following reagent vials:
(a) cyanide buffer pH 4.6
(b) acetate buffer pH 7.2
(c) phosphate buffer pH 7.2
(d) phosphate/hydroxide buffer
(e) albumin-coated charcoal.

We claim:
1. In a radioassay for vitamin $B_{12}$ wherein a serum or tissue extract sample is mixed with a known amount of radiolabeled vitamin $B_{12}$ and an intrinsic factor preparation, the intrinsic factor bound radiolabeled vitamin $B_{12}$ is separated from the unbound radiolabeled vitamin $B_{12}$, the amount of radiolabeled vitamin $B_{12}$ in the bound or unbound form is determined and compared to a standard curve obtained with samples of known, varying amounts of vitamin $B_{12}$ whereby the amount of vitamin $B_{12}$ in the sample can be determined, the improvement comprising using as said intrinsic factor preparation mouse or rat derived intrinsic factor.

2. The improved radioassay of claim 1 wherein said intrinsic factor preparation is mouse derived.

3. The improved radioassay of claim 1 wherein serum extract sample is obtained by extraction at about pH 4.5, and said assay is carried out at about pH 7.2.

4. The improved radioassay of claim 1 wherein said radiolabeled vitamin $B_{12}$ is $^{57}$Co-cyanocobalamin.

5. In a kit useful for carrying out radioassays for vitamin $B_{12}$ which kit comprises individual vials containing a solution of radiolabeled vitamin $B_{12}$, solutions of vitamin $B_{12}$ standards and an intrinsic factor preparation, the improvement comprising providing as said intrinsic factor preparation a mouse or rat derived intrinsic factor.

6. The improved kit of claim 5 wherein said intrinsic factor preparation is mouse derived intrinsic factor.

7. The improved kit of claim 5 wherein said kit contains as additional vials, a vial of cyanide extraction buffer pH 4.5 and a vial of phosphate buffer 7.2.

8. In a radioassay for vitamin $B_{12}$, wherein a serum or tissue extract sample is mixed with a known amount of radiolabeled vitamin $B_{12}$ and an intrinsic factor preparation, the intrinsic factor bound radiolabeled vitamin $B_{12}$ is separated from the unbound radiolabeled vitamin $B_{12}$, the amount of radiolabeled vitamin $B_{12}$ in the bound or unbound form is determined and compared to a sample curve obtained with samples of known, varying amounts of vitamin $B_{12}$, whereby the amount of vitamin $B_{12}$ in the sample can be determined, the improvement comprising using as said intrinsic factor preparation an extract derived from mammalian tissue which is free of R-protein.

* * * * *